US011464437B2

(12) United States Patent
Eliyahu et al.

(10) Patent No.: US 11,464,437 B2
(45) Date of Patent: Oct. 11, 2022

(54) MID-FIELD SIGNAL EXTRACTION

(71) Applicant: BIOSENSE WEBSTER (ISRAEL) LTD., Yokneam (IL)

(72) Inventors: Shiran Eliyahu, Yokneam Illit (IL); Vladimir Rubinstein, Haifa (IL); Limor Provizor, Lavon (IL); Elias Shamilov, Eshhar (IL); Herman-Eyal Lencovski, Kiriat-Yam (IL); Inbal Dubiner, Kazir (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 138 days.

(21) Appl. No.: 16/793,084

(22) Filed: Feb. 18, 2020

(65) Prior Publication Data
US 2020/0281494 A1 Sep. 10, 2020

Related U.S. Application Data

(60) Provisional application No. 62/814,532, filed on Mar. 6, 2019.

(51) Int. Cl.
*A61B 5/00* (2006.01)
*A61B 5/287* (2021.01)
*A61B 5/33* (2021.01)

(52) U.S. Cl.
CPC ............... *A61B 5/287* (2021.01); *A61B 5/33* (2021.01)

(58) Field of Classification Search
CPC ................................ A61B 5/287; A61B 5/339
(Continued)

(56) References Cited

U.S. PATENT DOCUMENTS 6,226,542 B1 5/2001 Reisfeld
6,301,496 B1 10/2001 Reisfeld
(Continued)

FOREIGN PATENT DOCUMENTS

| EP | 3033993 A2 * | 6/2016 | ......... A61B 18/1206 |
| EP | 3033993 A2 | 6/2016 | |
| WO | WO2018069509 A1 | 4/2018 | |

OTHER PUBLICATIONS

European Search Report for corresponding EPA No. 20161214.0 dated May 11, 2020.

*Primary Examiner* — Nicole F Lavert
(74) *Attorney, Agent, or Firm* — Dergosits & Noah LLP; Todd A. Noah

(57) ABSTRACT

A medical analysis system, includes at least one catheter to be inserted into a body-part having a tissue surface, and comprising sensing electrodes to contact and receive electrical signals from the tissue surface, and processing circuitry to receive unipolar signals from individual ones of the plurality of the sensing electrodes, compute a combined far-field and mid-field signal based on summing and filtering ones of the received unipolar signals received from at least a pair of sensing electrodes disposed around a point of interest, compute a far-field signal as a weighted average of the received unipolar signals, weighted according to respective distances of the sensing electrodes from the point of interest, and compute and output a mid-field signal, representative of electrical activity below the tissue surface at the point of interest, based on subtracting the computed far-field signal from the computed combined far-field and mid-field signal.

20 Claims, 4 Drawing Sheets

(58) Field of Classification Search
USPC .......................................................... 600/509
See application file for complete search history.

(56) References Cited

U.S. PATENT DOCUMENTS

| | | |
|---|---|---|
| 6,892,091 B1 | 5/2005 | Ben |
| 2005/0197586 A1 | 9/2005 | Pearlman |
| 2009/0099468 A1 | 4/2009 | Thiagalingam |
| 2014/0005664 A1 | 1/2014 | Govari |
| 2014/0187991 A1 | 7/2014 | Thakur |
| 2016/0338611 A1* | 11/2016 | Kalinin ................ A61B 5/6805 |
| 2018/0279896 A1* | 10/2018 | Ruppersberg ........ A61B 5/6857 |
| 2019/0126050 A1* | 5/2019 | Shuros ............... A61N 1/36521 |

* cited by examiner

MID-FIELD SIGNAL EXTRACTION

RELATED APPLICATION INFORMATION

The present application claims the benefit of U.S. Provisional Patent Application No. 62/814,532 of Eliyahu, et al., filed on Mar. 6, 2019.

FIELD OF THE INVENTION

The present invention relates to cardiac electrical activity, and in particular, to computing cardiac signals.

BACKGROUND

Electrical activity at a point in the heart may be measured by advancing a multiple-electrode catheter to measure electrical activity at multiple points in the heart chamber simultaneously. Other methods, such as using an external vest may provide an indication of cardiac activity. A record derived from time varying electrical potentials as measured by one or more electrodes is known as an electrogram. Electrograms may be measured by unipolar or bipolar leads, and are used, e.g., to determine the onset of electrical propagation at a point, known as local activation time (LAT).

Electrode sensors in a cardiac chamber may detect far-field electrical activity, i.e., the ambient electrical activity originating away from the sensors, which can distort or obscure local electrical activity, i.e., signals originating at or near the sensors. Commonly assigned U.S. Patent Application Publication No. 2014/0005664 to Govari et al., discloses distinguishing a local component in an intracardiac electrode signal, due to the tissue with which the electrode is in contact from a remote-field contribution to the signal, and explains that a therapeutic procedure applied to the tissue can be controlled responsively to the distinguished local component.

US Patent Publication 2005/0197586 to Pearlman describes a method of, and system for, signal separation during multivariate physiological monitoring. Multiple electrode contacts make electrical connections to the anterior and/or posterior chest for multivariate characterization of the electrical activation of the heart. A central processing unit derives synthetic composite electrographic signals as well as flag signals for specific purposes. An embodiment uses this system to trigger or gate magnetic resonance imaging, eliminating or reducing problems from small or inverted R-waves, lead detachment, noise, flow signal, gradient changes, and rhythm changes, more reliably flagging the onset of electrical activation of the ventricles. Additional derived data are ST-segment shifts, filling times, and respiratory cycle. Filling times may be used for greatly improved imaging in the presence of rhythm disturbances, such as atrial fibrillation. Respiratory cycle may be used as a respiratory trigger to control for the effects of breathing on the heart position and image quality.

US Patent Publication 2009/0099468 to Thiagalingam, et al., describes a method, an apparatus, and a computer program product for automated processing of intracardiac electrophysiological data. The method comprises the steps of: recording electrogram data and corresponding spatial location data of an electrode recording the electrogram data, the recorded electrogram data comprising a plurality of beats; defining at least one reference channel containing a reference beat for determining temporal locations and against which beats of the recorded electrogram data are compared; examining the recorded electrogram data and defining a temporal location for each beat of the recorded electrogram data; creating an index of the temporal locations and other information of the beats within the recorded electrogram data; analyzing in real-time at least one electrophysiological feature of the recorded electrogram data suggestive of a physiological condition; and providing an updated index wherein the other information comprises results of the analysis.

SUMMARY

There is provided in accordance with an embodiment of the present invention, a medical analysis system, including at least one catheter configured to be inserted into a body-part having a tissue surface, and including a plurality of sensing electrodes configured to contact and receive electrical signals from the tissue surface, and processing circuitry configured to receive unipolar signals from individual ones of the plurality of the sensing electrodes, compute a combined far-field and mid-field signal based on summing and filtering ones of the received unipolar signals received from at least a pair of the plurality of sensing electrodes, the at least a pair of the sensing electrodes being disposed around a point of interest, compute a far-field signal as a weighted average of the received unipolar signals, weighted respective distances of the sensing electrodes from the point of interest, and compute and output a mid-field signal, representative of electrical activity below the tissue surface at the point of interest, based on subtracting the computed far-field signal from the computed combined far-field and mid-field signal.

Further in accordance with an embodiment of the present invention the processing circuitry is configured to apply a high-pass filter to the sum of the received unipolar signals received from the at least a pair of the sensing electrodes.

Still further in accordance with an embodiment of the present invention the processing circuitry is configured to select a plurality of electrode groups from the sensing electrodes, sum, for each one electrode group of the plurality of electrode groups, the unipolar signals received from the one electrode group, yielding a plurality of summed group signals, and compute the weighted average based on averaging the summed group signals weighted respective distances of the sensing electrodes from the point of interest.

Additionally, in accordance with an embodiment of the present invention the processing circuitry is configured to apply a high-pass filter to each of the summed group signals prior to computing the weighted average.

Moreover, in accordance with an embodiment of the present invention the processing circuitry is configured to render the mid-field signal to a display.

Further in accordance with an embodiment of the present invention the processing circuitry is configured to render a map to a display based on electrical activity of the mid field signal at various locations on the tissue surface.

Still further in accordance with an embodiment of the present invention the processing circuitry is configured to output a diagnostic decision based on at least one characteristic of the mid-field signal.

Additionally, in accordance with an embodiment of the present invention the tissue surface includes any of the following an endocardial tissue surface, an epicardial tissue surface, and an organ tissue surface.

There is also provided in accordance with another embodiment of the present invention, a electrophysiological analysis method, including receiving unipolar signals from individual ones of a plurality of the sensing electrodes of at least one catheter configured to be inserted into a body-part having a tissue surface, the sensing electrodes being configured to contact and receive electrical signals from the tissue surface, computing a combined far-field and mid-field signal based on summing and filtering ones of the received unipolar signals received from at least a pair of the plurality of sensing electrodes, the at least a pair of sensing electrodes being disposed around a point of interest, computing a far-field signal as a weighted average of the received unipolar signals, weighted respective distances of the sensing electrodes from the point of interest, and computing and outputting a mid-field signal, representative of electrical activity below the tissue surface at the point of interest, based on subtracting the computed far-field signal from the computed combined far-field and mid-field signal.

Moreover, in accordance with an embodiment of the present invention, the method includes applying a high-pass filter to the sum of the received unipolar signals received from the at least a pair of the sensing electrodes.

Further in accordance with an embodiment of the present invention, the method includes selecting a plurality of electrode groups from the sensing electrodes, summing, for each one electrode group of the plurality of electrode groups, the unipolar signals received from the one electrode group, yielding a plurality of summed group signals, and computing the weighted average based on averaging the summed group signals weighted respective distances of the sensing electrodes from the point of interest.

Still further in accordance with an embodiment of the present invention, the method includes applying a high-pass filter to each of the summed group signals prior to computing the weighted average.

Additionally, in accordance with an embodiment of the present invention, the method includes rendering the mid-field signal to a display.

Moreover, in accordance with an embodiment of the present invention, the method includes rendering a map to a display based on electrical activity of the mid field signal at various locations on the tissue surface.

Further in accordance with an embodiment of the present invention, the method includes outputting a diagnostic decision based on at least one characteristic of the mid-field signal.

Still further in accordance with an embodiment of the present invention the tissue surface includes any of the following an endocardial tissue surface, an epicardial tissue surface, and an organ tissue surface.

There is also provided in accordance with still another embodiment of the present invention a software product, including a non-transient computer-readable medium in which program instructions are stored, which instructions, when read by a central processing unit (CPU), cause the CPU to receive unipolar signals from individual ones of a plurality of the sensing electrodes of at least one catheter configured to be inserted into a body-part having a tissue surface, the sensing electrodes being configured to contact and receive electrical signals from the tissue surface, compute a combined far-field and mid-field signal based on summing and filtering ones of the received unipolar signals received from at least a pair of the plurality of sensing electrodes, the at least a pair of the sensing electrodes being disposed around a point of interest, compute a far-field signal as a weighted average of the received unipolar signals, weighted respective distances of the sensing electrodes from the point of interest, and compute and output a mid-field signal, representative of electrical activity below the tissue surface at the point of interest, based on subtracting the computed far-field signal from the computed combined far-field and mid-field signal.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
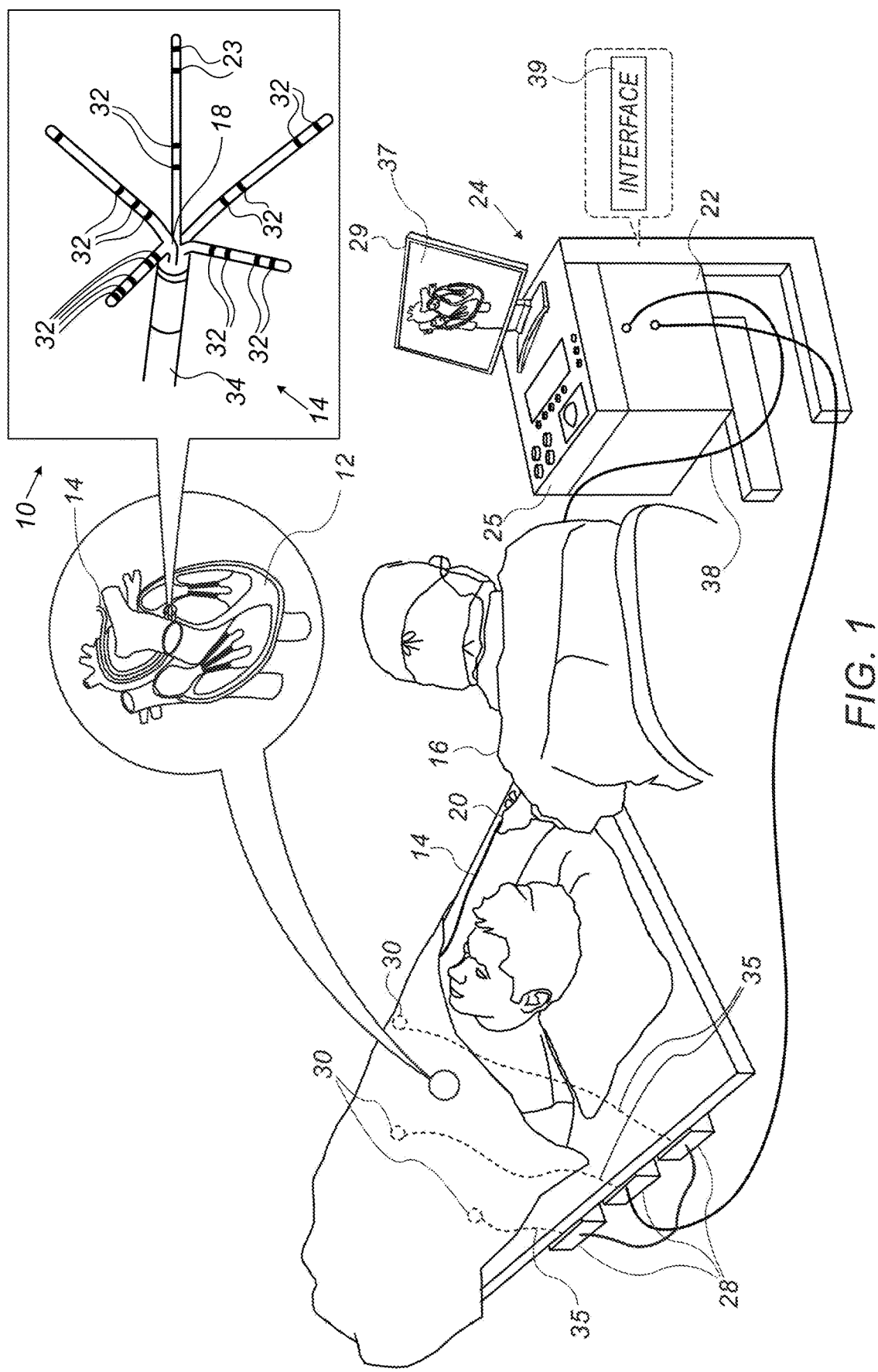
FIG. 1 is a partly pictorial, partly block diagram view of a cardiac analysis system constructed and operative in accordance with an embodiment of the present invention.

In thick tissue, such as the ventricle, electricity is conducted throughout the different layers of the endocardium and myocardium. After performing an ablation (from the endocardial or the epicardial side), it may be necessary to measure the electrical activity beneath the ablation surface in a region of interest because residual conduction is generally a sign of insufficient ablation. Checking for residual conduction may be particularly important for treatment of ventricular tachycardia, by way of example only.

Electrodes in a cardiac chamber may detect surface electrical activity based on a bipolar signal received from the electrodes. Unipolar signals received from the electrodes are generally indicative of the surface activity and sub-surface activity. However, the unipolar signals also include far-field electrical activity, i.e., the ambient electrical activity originating away from the electrodes originating in the surrounding tissue, which can distort or obscure local electrical activity, i.e., signals originating at or near the electrodes. For the sake of notational convenience, the surface electrical activity and the sub-surface activity are described herein as exhibiting a near-field signal and a mid-field signal, respectively.

Therefore, although near-field and total electrical field signals may be deduced from the bipolar and unipolar signals, respectively, the mid-field signal does not appear to be directly measurable apart from providing epicardial access, in addition to endocardial access, for example, by puncturing the chest, to measure the sub-surface signals. However, puncturing the chest is both cumbersome and dangerous, and may require additional medical professionals from different disciplines and may prolong the procedure.

Exemplary embodiments of the present invention provide a system and method to compute the mid-field signal for a point of interest based on unipolar signals from sensing electrodes of one or more catheters inserted into a body-part (e.g., chamber of a heart or any other organ or body-part) without the need for additional access (e.g., epicardial or endocardial access).

The DC component is generally extracted from each unipolar signal to remove artifacts and a low pass filter is optionally applied to each unipolar signal to remove high frequency noise before the processing described below.

A combined far-field and mid-field signal is computed based on summing and filtering the unipolar signals of a sensing electrode pair of the sensing electrodes. The sensing electrode pair is disposed around the point of interest. The filtering includes applying a high pass filter to the summed signal. The high pass filter used here and mentioned below removes a near-field component from the signal.

A far-field signal is computed as a weighted average of the received unipolar signals, weighted according to respective distances of the sensing electrodes from the point of interest. The averaging tends to remove a mid-field component of the signals while leaving the far-field component. Computation of the weighted average may be computed as follows. A plurality of electrode pairs is selected from the sensing electrodes and for each electrode pair, the unipolar signals are summed yielding a plurality of summed pair signals. A high-pass filter is applied to each of the summed pair signals prior to computing the weighted average. The weighted average is computed based on averaging the summed pair signals weighted according to the respective distances of the sensing electrode pairs from the point of interest.

In some exemplary embodiments, the above processing mentioned above with respect to the sensing electrode pair may be performed using an electrode group of three or more electrodes disposed around the point of interest. Similarly, the processing mentioned above with respect to the plurality of electrode pairs mentioned above may be performed with a plurality of electrode groups, each group having three or more electrodes.

The mid-field signal, representative of electrical activity below the tissue surface at the point of interest, is computed based on subtracting the computed far-field signal from the computed combined far-field and mid-field signal.

The computed mid-field signal or a map based on electrical activity of the mid-field signal at various locations on the tissue surface may be output to a display. In some exemplary embodiments at least one characteristic of the mid-filed signal may be used to determine a diagnostic decision, for example, whether (additional) ablation should be performed, and if so for how long, by way of example only. The diagnostic decision may also be output to the display.

The mid-field may be used to determine if a previously ablated region or a scarred sick region requires ablation due to discovered sub-surface electrical activity. Additionally, or alternatively, the mid-field signal may be used to map the heart of a patient to diagnose the patient and determine what treatment is needed (e.g., where to ablate and for how long).

It should be noted that for the sake of simplicity the exemplary embodiments described herein generally describe performing an ablation from the endocardial surface and computing the mid-field signal below the endocardial surface. Exemplary embodiments of the invention may also include performing an ablation from the epicardial surface and computing the mid-field signal below the epicardial surface.

Additionally, example embodiments describe computation of a midfield signal for a heart chamber. Other embodiments may include computing a midfield signal for any living tissue, e.g., intestinal tract, based on applying suitable modifications to the embodiments described herein.

System Description

Reference is now made to FIG. 1, which is a partly pictorial, partly block diagram view of a cardiac analysis system 10 constructed and operative in accordance with an exemplary embodiment of the present invention.

Turning now to the drawings, reference is initially made to FIG. 1, which is a pictorial illustration of a cardiac analysis system 10, constructed and operative in accordance with a disclosed exemplary embodiment of the present invention, for computing and evaluating electrical activity and optionally for performing ablative procedures on a heart 12 of a living subject. The system comprises a catheter 14, such as a catheter, which is percutaneously inserted by an operator 16 through the patient's vascular system into a chamber or vascular structure of the heart 12. The operator 16, who is typically a physician, brings a distal tip 18 of the catheter 14 into contact with the heart wall, for example, at an ablation target site or to capture electrical potentials over time at multiple sample location over a surface of one or more chambers of the heart 12. Electrical activation maps may be prepared, according to the methods disclosed in U.S. Pat. Nos. 6,226,542, and 6,301,496, and in commonly assigned U.S. Pat. No. 6,892,091. One commercial product embodying elements of the system 10 is available as the CARTO® 3 System, available from Biosense Webster, Inc., 33 Technology Drive, Irvine, Calif. 92618 USA. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a temperature (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal tip 18 of the catheter 14 as desired for the ablation. To aid the operator 16, a distal portion of the catheter 14 contains position sensors (not shown) that provide signals, via a cable 38, to processing circuitry 22, located in a console 24. The processing circuitry 22 may fulfill several processing functions as described below.

Ablation energy and electrical signals can be conveyed to and from the heart 12 through electrodes 32 located at or near the distal tip 18 via cable 38 (and a shaft 34 of the catheter 14) to the console 24. In such a manner, the electrodes 32 are configured to capture electrical potentials over time at multiple sample locations over a surface of one or more chambers of the heart 12. Additionally, or alternatively, other electrodes may be configured to capture electrical potentials over time at multiple sample locations over a surface of one or more chambers of the heart 12. Pacing signals and other control signals may be conveyed from the console 24 through the cable 38 and the electrodes 32 to the heart 12. The catheter 14 may be implemented without ablation capabilities as an exploratory device having electrodes configured to capture electrical potentials over time at multiple sample locations over a surface of one or more chambers of the heart 12.

Wire connections 35 link the console 24 with body surface electrodes 30 and other components of a positioning sub-system for measuring location and orientation coordinates of the catheter 14. The processing circuitry 22 or another processor (not shown) may be an element of the positioning sub-system. The electrodes 32 and the body surface electrodes 30 may be used to measure tissue impedance at the ablation site as taught in U.S. Pat. No. 7,536,218, issued to Govari et al. A sensor for bioelectric information, e.g., a temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816.

In one exemplary embodiment, the positioning subsystem comprises a magnetic position tracking arrangement that determines the position and orientation of the catheter 14 by generating magnetic fields in a predefined working volume and sensing these fields at the catheter 14, using field generating coils 28. The positioning subsystem is described in U.S. Pat. No. 7,756,576, and in the above-noted U.S. Pat. No. 7,536,218.

As noted above, the catheter 14 is coupled to the console 24, which enables the operator 16 to observe and regulate the functions of the catheter 14. The processing circuitry 22 may be embodied as a computer with appropriate signal processing circuits. The processing circuitry 22 is coupled to drive a monitor 29 including a display screen 37. The signal processing circuits may receive, amplify, filter and digitize signals from the catheter 14, including signals generated by sensors such as electrical, temperature and contact force sensors, and location sensing electrodes (not shown) located distally in the catheter 14. The digitized signals are received and used by the console 24 and the positioning sub-system to compute the position and orientation of the catheter 14, and to analyze the electrical signals from the electrodes.

In order to generate electroanatomic maps, the processing circuitry 22 typically comprises an electroanatomic map generator, an image registration program, an image or data analysis program and a graphical user interface configured to present graphical information on the monitor 29.

In practice, some or all of these functions of the processing circuitry 22 may be combined in a single physical component or, alternatively, implemented using multiple physical components. These physical components may comprise hard-wired or programmable devices, or a combination of the two. In some exemplary embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The console 24 may also include an interface 39 to receive input commands from the operator 16 via any suitable user input device, for example, but not limited to, a pointing device (such as a mouse of stylus), a keyboard, and/or a touch sensitive screen implemented in the display screen 37.

Typically, the system 10 includes other elements, which are not shown in the figures for the sake of simplicity. For example, the system 10 may include an electrocardiogram (ECG) monitor, coupled to receive signals from the body surface electrodes 30, in order to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 and maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in, or invoked by, the processing circuitry 22 for generating and displaying images.

Figure 2A:
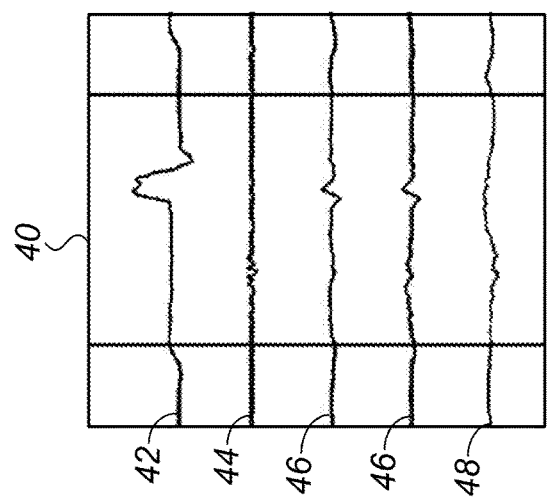
FIGS. 2A-C are views of cardiac signals provided by the system of FIG. 1.
Figure 2B:
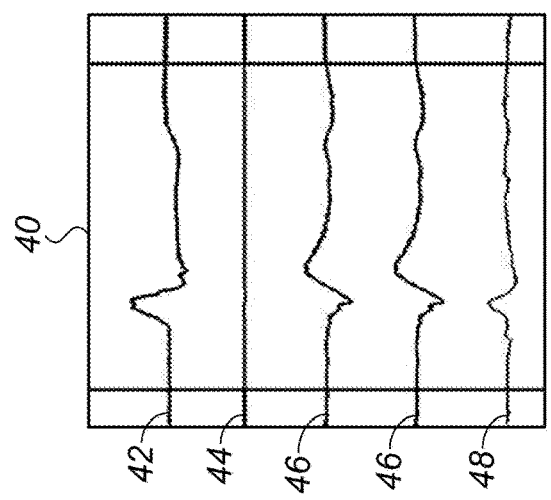
Figure 2C:
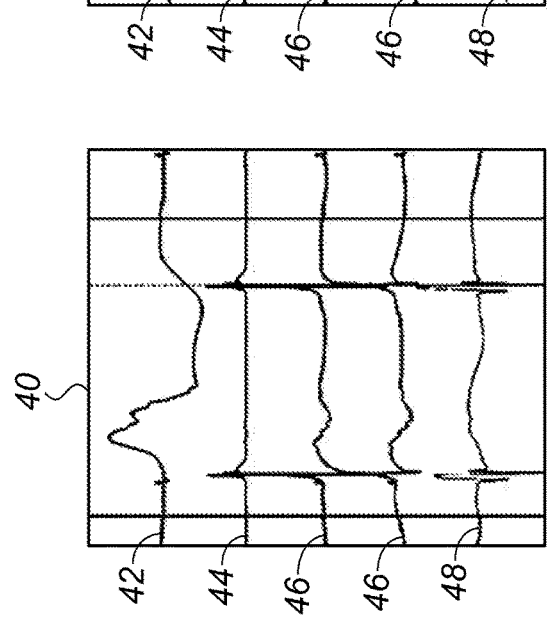

Reference is now made to FIGS. 2A-C, which are views of cardiac signals in a signal display 40 provided by the system 10 of FIG. 1. Each of the FIGS. 2A-C shows a body surface (BS) signal 42, a bipolar signal 44, two unipolar signals 46, and a computed mid-field signal 48.

The signal 42 represents body surface behavior and in FIGS. 2A-C generally indicates that the heart 12 is beating. The bipolar signal 44 is typically received from a pair of electrodes of the catheter 14 and is representative of surface, or close-to-surface, near-field electrical activity. Each of the unipolar signals 46 may be individually received from the same two electrodes that provide the bipolar signal 44. The mid-field signal 48 is computed as will be described in more detail with reference to FIG. 6.

FIG. 2A shows signals 42-48 which indicate that the region of the heart (the point of interest) 12 being probed is healthy.

In FIG. 2B, the bipolar signal 44 is flat indicating that the near-field or surface electrical activity is dead. However, the unipolar signals 46 shows that there is still electrical activity being detected. The detected electrical activity may be from the far-field and possibly from the mid-field. The computed mid-field signal 48 indicates that the unipolar signals 46 indeed include a component from the mid-field and that there is electrical activity in the sub-surface of the myocardium and in the epicardium. In such a case, further ablation may be warranted.

In FIG. 2C, the bipolar signal 44 is flat indicating that the near-field or surface electrical activity is dead. However, the unipolar signals 46 shows that there is still some electrical activity being detected. The detected electrical activity may be from the far-field and possibly from the mid-field. The computed mid-field signal 48 which is fairly flat indicates that the unipolar signals 46 do not include a component from the mid-field and that there is no electrical activity in the sub-surface of the myocardium and in the epicardium. In such a case, further ablation is generally not required.

A cut-off limit may be set to determine if the mid-field signal 48 of the region of interest represents electrical activity of the sub-surface of the myocardium and in the epicardium. By way of example, the limit may be set to equal 5 milli Volts (mV) or any suitable value so that a value above 5 mV represents live heart tissue and below 5 mV represents dead heart tissue.

Figure 3A:
FIGS. 3A-C are views of mid-field signals provided by the system of FIG. 1.
Figure 3B:
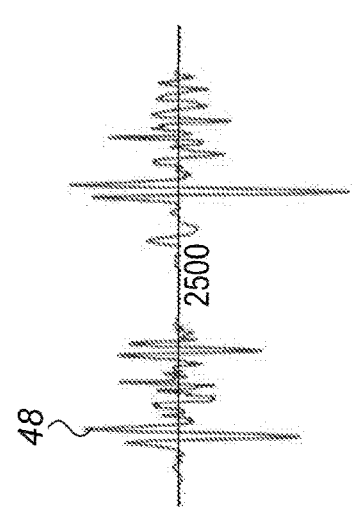
Figure 3C:
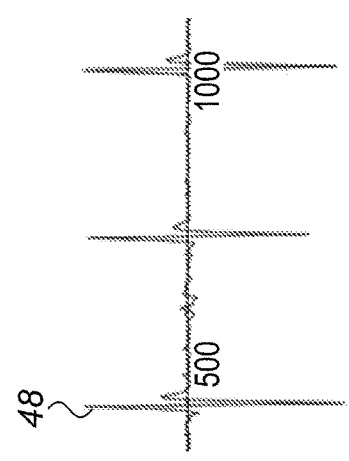

Reference is now made to FIGS. 3A-C, which are views of mid-field signals 48 provided by the system of FIG. 1. FIG. 3A shows an exemplary mid-field signal 48 of healthy tissue. FIG. 3B shows an exemplary mid-field signal 48 of sick tissue. FIG. 3C shows an exemplary mid-field signal 48 of dead tissue.

Figure 4:
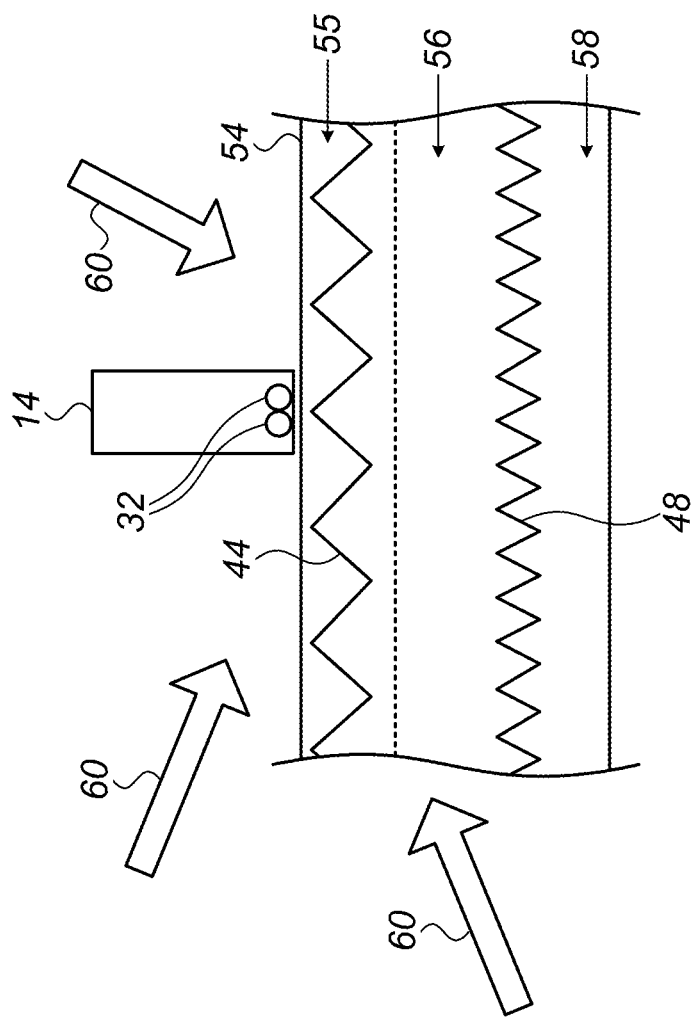
FIG. 4 is a schematic view of a cross-section of heart tissue illustrating cardiac electrical activity.

Reference is now made to FIG. 4, which is a schematic view of a cross-section of heart tissue 54 illustrating cardiac electrical activity as well as ambient electrical activity 60 originating away from the electrodes 32. The heart tissue 54 includes an endocardium 55, a myocardium 56 and an epicardium 58. The multi-electrode catheter 14 is shown schematically in FIG. 4 with two sensing electrodes 32 for the sake of simplicity. The multi-electrode catheter 14 may include any suitable number of sensing electrodes 32. In some embodiments, the catheter 14 may include groups of three or more sensing electrodes. The two sensing electrodes 32 are positioned at the point of interest and may provide the near field signal 44 representative of the electrical activity at the surface and just below the surface of the heart tissue 54. Each of the sensing electrodes 32 may also provide a unipolar signal which measures combined electrical activity at the point of interest from various distances (e.g., the electrical activity may include near, mid and far-field activity).

FIG. 4 illustrates that the catheter 14 cannot directly measure the mid-field signal 48. The mid-field signal 48 is computed based on a suitable selection of sensing electrode signals surrounding the electrodes 32 positioned at the point of interest, described in more detail with reference to FIGS. 5-6.

Figure 5:
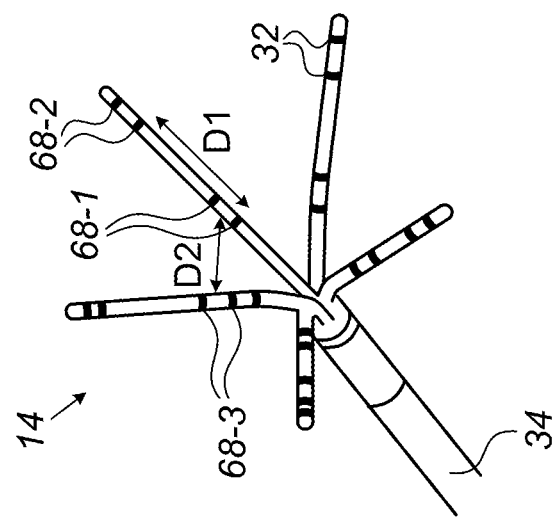
FIG. 5 is a schematic view of a catheter for use in the system of FIG. 1.

Reference is now made to FIG. 5, which is a schematic view of the multi electrode catheter 14 for use in the system 10 of FIG. 1. In accordance with some exemplary embodiments, the catheter 14 performs electrical activity mapping without performing ablation. The catheter 14 is configured to be inserted into a chamber of the heart 12 or other body-part, and includes the shaft 34 and the plurality of sensing electrodes 32 configured to contact and receive electrical signals from a tissue surface (e.g., an endocardium tissue surface or an epicardium tissue surface or any other suitable tissue surface of any suitable organ or body-part). The sensing electrodes 32 may be arranged in sensing electrode pairs or groups of three or more electrodes in each group. For the sake of simplicity, three of the sensing electrode pairs 68 are labeled in FIG. 3, for example, the pairs 68-1, 68-2, and 68-3.

Any suitable catheter or catheters (of any suitable shape) with multiple electrodes may be used to provide data for the computation described below with reference to FIG. 6. For example, the multiple electrodes used to provide the data may be part of more than one catheter inserted into the body part. FIG. 5 shows a schematic view of the Pentaray® catheter commercially available from Biosense Webster. Other catheters may also be used for example, but not limited to, the Octaray® catheter of Biosense Webster, or any other suitable catheter, for example, but not limited to, a balloon-shaped catheter or a lasso-shaped catheter.

Figure 6:
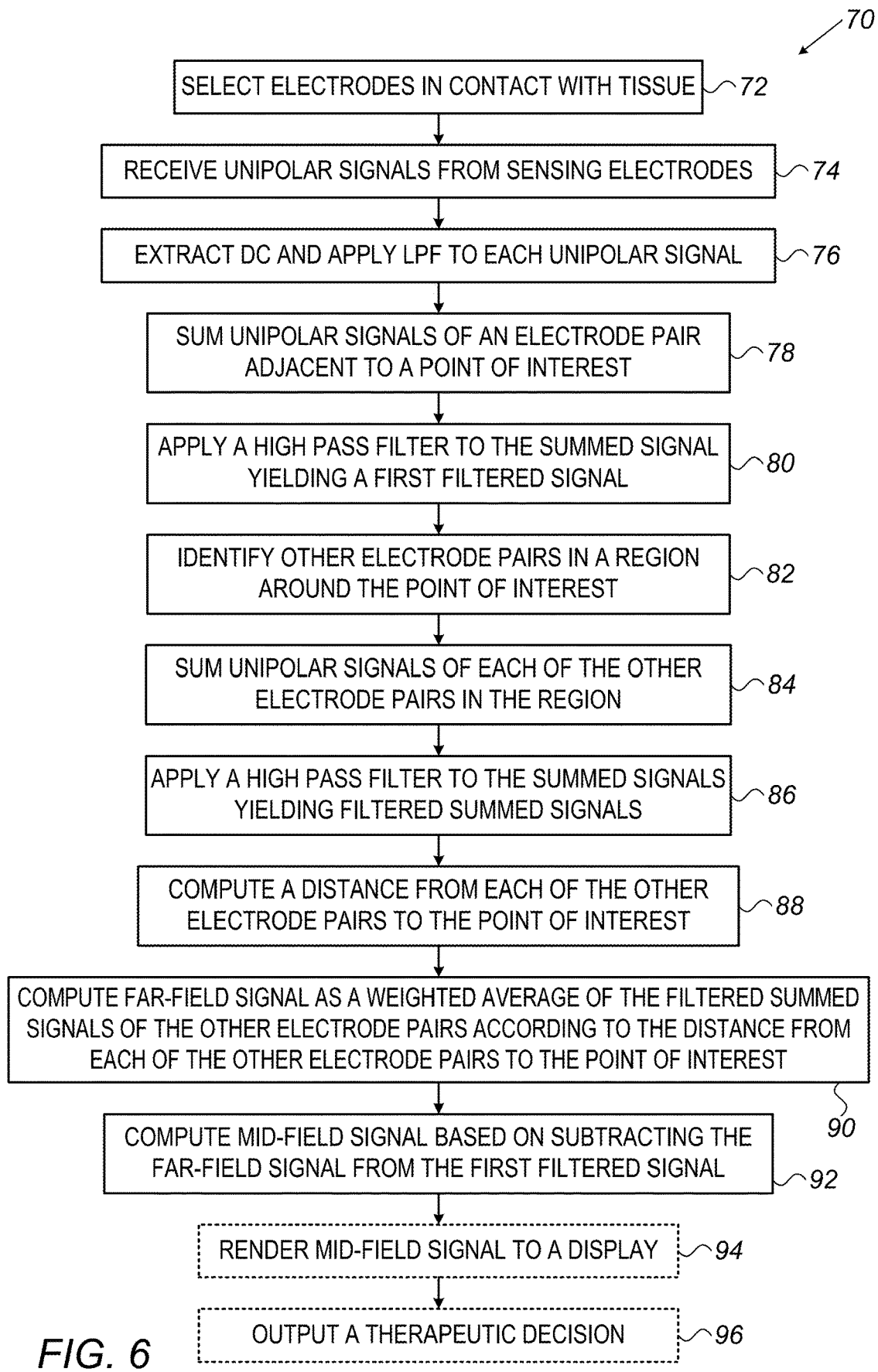
FIG. 6 is a flowchart including exemplary steps in a method of operation of the system of FIG. 1.

Reference is now made to FIG. 6, which is a flowchart 70 including exemplary steps in a method of operation of the system 10 of FIG. 1. Reference is also made to FIG. 5.

The description below refers to using electrode pairs 68. In some exemplary embodiments, the steps mentioned below with respect to the sensing electrode pair 68-1 may be performed using an electrode group of three or more electrodes disposed around the point of interest. Similarly, the steps mentioned below with respect to the plurality of electrode pairs (e.g., the pairs 68-2 and 68-3) may be performed with a plurality of electrode groups, each group having three or more electrodes.

The processing circuitry 22 is configured to select (block 72) the sensing electrodes 32 that are in contact with the heart tissue 54 (FIG. 4) from which to receive unipolar signals 46. The sensing electrodes 32 that are not in contact with the heart tissue 54 generally do not provide unipolar signals that are representative of the electrical activity of the heart tissue 54.

The processing circuitry 22 is configured to receive (block 74) unipolar signals 46 (FIG. 2A-C) from individual ones of the selected sensing electrodes 32.

The processing circuitry 22 is optionally configured to extract (block 76) a DC component and a low pass filter to each of the received unipolar signals 46 in order to remove artifacts and reduce noise in the unipolar signals 46. The signals used in the method described below have already has the DC component removed and generally the low pass filter applied.

The mid-field signal 48, $ECG_{quad}(k, i)$, may be computed according to the following equation:

$$ECG_{quad}(k, i) = HPF[Uni(k) + Uni(k+1)] - \sum_{i=1}^{n} w(d_{k,i}) \times HPF[Uni(i) + Uni(i+1)] \quad \text{(equation 1)}$$

and $w(d_{k,i})$ may be computed from the following equation:

$$w(d_{k,i}) = \frac{1}{d_{k,i}} \times \frac{\sum_{m=1}^{n} d_{k,m}}{\prod_{m=1}^{n} d_{k,m}} \quad \text{(equation 2)}$$

where k and k+1 is the pair of electrodes positioned in the point of interest, i are representative of electrode pairs positioned in the environment of point of interest, $w(d_{k,i})$ is the weight for the $i^{th}$ electrode pair 68 and is inversely proportional to the distance $d_{k,i}$ between the $k^{th}$ electrode pair 68 and the ith electrode pair 68, n is the number of electrode pairs 68 used in the weighted average computation, m is an index used in equation 2, HPF is a high-pass filter, Uni(k) is the unipolar signal 46 of the $k^{th}$ sensing electrode 68, and Uni(i) is the unipolar signal 46 of the $i^{th}$ sensing electrode 68.

It should be noted that in equation 1, shown above, the second term including the summation from i=1 to n is performed with a step of 2, so that an initial value of i is equal to 1, a second value of i is equal to 3, and so on.

Equation 1 may be suitably modified when groups of three electrodes are used instead of electrode pairs. For example, if there are three electrodes per group:

$$ECG_{quad}(k, i) = HPF[Uni(k) + Uni(k+1) + Uni(k+2)] - \sum_{i=1}^{n} w(d_{k,i}) \times HPF[Uni(i) + Uni(i+1) + Uni(i+2)]$$

It should be noted that in equation 1, shown immediately above, the second term including the summation from i=1 to n is performed with a step of 3, so that an initial value of i is equal to 1, a second value of i is equal to 4, and so on. In general, the size of the step is equal to the number of unipolar signals listed in the second term of equation 1.

Computation of the mid-field signal 48 using equation 1 is now described in more detail.

Computation of the first term, HPF[Uni(k)+Uni(k+1)], in equation 1 is now described in more detail.

The processing circuitry 22 is configured to sum (block 78) unipolar signals 46 of a pair (e.g. the pair 68-1) of the sensing electrodes 32 that are located adjacent to the point of interest. The sensing electrodes 32 of the pair 68-1 are cited by way of example. Any pair of the sensing electrodes 32 may be used thereby defining a central location of the point of interest which is located between the electrodes of the selected electrode pair. Summing the unipolar signals 46 results in enhancing the signal prior to applying the high-pass filter described below in the step of block 80.

The processing circuitry 22 is configured to apply (block 80) a high-pass filter to the summed signal computed in the step of block 78 yielding a filtered signal representative of a combination of the far-field signal and the mid-field signal 48. The high-pass filter weakens slow elements, e.g. the near field.

Therefore, in the steps of blocks 78 and 80, the processing circuitry 22 computes a combined far-field and mid-field signal based on: summing a pair of the received unipolar signals received from the sensing electrode pair disposed around a point of interest; and then filtering the summed signal.

Computation of the second term, $w(d_{k,i}) \times HPF[Uni(i)+Uni(i+1)]$, in equation 1 is now described in more detail. The processing circuitry 22 is configured to identify or select (block 82) other electrode pairs 68 from the sensing electrodes 32 for use in computing the second term of the equation.

The processing circuitry 22 is configured to sum (block 84), for each electrode pair 68 (selected in the step of block 82), the unipolar signals 46 received from that electrode pair 68, yielding a plurality of summed paired signals. By way of example, the unipolar signals 46 of the pair 68-2 are summed, and the unipolar signals 46 of the pair 68-3 are summed, etc.

The processing circuitry 22 is configured to apply (block 86) a high-pass filter to each of the summed pair signals prior to computing the weighted average described below.

The processing circuitry 22 is configured to compute (block 88) a distance from (a mid-point of) each pair 68 to the point of interest. By way of for example, the processing circuitry 22 computes the distance D1 for the pair 68-2 and D2 for the pair 68-3, and so on. The distance between the relevant electrode or electrode pairs may be computed based on a known geometry of the catheter 14 or based on position tracking of the sensing electrodes 32 using any suitable position tracking, for example, using impedance-based position measurements or based on a scanned image.

The computed distances may then be used to compute $w(d_{k,i})$ using the equation given above or based on any other suitable statistical method. For example, the weight applied to the unipolar signals of the sensing electrodes 32 in the pair 68-2 is inversely proportional to a distance D1 from the pair 68-2 to the pair 68-1, and the weight applied to the unipolar signals of the sening e ectrodes 32 in the pair 68-3 is inversely proportional to a distance D2 from the pair 68-3 to the pair 68-1.

The processing circuitry 22 is configured to compute (block 90) a far-field signal as a weighted average of the summed paired (and filtered) unipolar signals processed in the steps of blocks 84 and 86. The weighted average may be weighted according to respective distances of the sensing electrodes 32 from the point of interest (e.g., of the pair 68-1) using the weight $w(d_{k,i})$ by way of example only. Weighting the average provides improved accuracy in computing the far-field signal as the far field detected by one sensing electrode 32 is generally slightly different from the far field detected by another of the sensing electrodes 32. Therefore, the weighted average provides more weight to signals closer to the point of interest to take into account the difference in the far field measured at different positions.

The processing circuitry 22 is configured to compute (block 92) a mid-field signal, representative of electrical activity below the tissue surface at the point of interest, based on subtracting the computed far-field signal (the second term of equation 1) from the computed combined far-field and mid-field signal (the first term of equation 1).

The processing circuitry 22 is optionally configured to render (block 94) one or more of the following: the bipolar signal 44, the unipolar signals 46, and/or the mid-field signal 48, to the display screen 37 (FIG. 1). Additionally, or alternatively, the processing circuitry 22 is configured to render a map to the display screen based on electrical activity of the mid field signal at various locations on the tissue surface.

The processing circuitry 22 is configured to output (block 96) a diagnostic decision based on at least one characteristic (e.g., magnitude) of the mid-field signal 48. The diagnostic decision may include, for example, whether (additional) ablation should be performed, and if so for how long, by way of example only. The diagnostic decision may also be output to the display screen 37. A cut-off limit may be set to determine if the mid-field signal 48 of the point of interest represents electrical activity of the sub-surface of the myocardium and in the epicardium. By way of example, the limit may be set to equal 0.5 mV or any suitable value so that a value above 0.5 mV represents live tissue and below 0.5 mV represents dead tissue.

The mid-field may be used to determine if a previously ablated region requires more ablation due to discovered sub-surface electrical activity. Additionally, or alternatively, the mid-field signal may be used to map the heart of a patient to diagnose the patient and determine what treatment is needed (e.g., where to ablate and for how long). For example, to diagnose ischemic heart tissue and differentiate whether the tissue is scarred throughout its depth or whether there are conducting regions.

The equation described above is cited by way of example only and any suitable equation may be used instead. The equation described above may be amended to include additional terms, or constants by way of example only.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:
1. A medical analysis system, comprising:
at least one catheter configured to be inserted into a body-part having a tissue surface, and comprising a plurality of sensing electrodes configured to contact and receive electrical signals from the tissue surface; and
processing circuitry configured to:

receive unipolar signals from individual ones of the plurality of the sensing electrodes;

compute a combined far-field and mid-field signal based on summing and filtering the received unipolar signals from at least a pair of the plurality of sensing electrodes, the at least a pair of the sensing electrodes being disposed around a point of interest;

compute a far-field signal as a weighted average of the received unipolar signals, weighted according to respective distances of the sensing electrodes from the point of interest; and compute and output a mid-field signal, representative of electrical activity below the tissue surface at the point of interest, based on subtracting the computed far-field signal from the computed combined far-field and mid-field signal.

2. The system according to claim 1, wherein the processing circuitry is configured to apply a high-pass filter to the sum of the received unipolar signals received from the at least a pair of the sensing electrodes.

3. The system according to claim 1, wherein the processing circuitry is configured to:

select a plurality of electrode groups from the sensing electrodes;

sum, for each one electrode group of the plurality of electrode groups, the unipolar signals received from the one electrode group, yielding a plurality of summed group signals; and compute the weighted average based on averaging the summed group signals weighted according to respective distances of the sensing electrodes from the point of interest.

4. The system according to claim 3, wherein the processing circuitry is configured to apply a high-pass filter to each of the summed group signals prior to computing the weighted average.

5. The system according to claim 1, wherein the processing circuitry is configured to render the mid-field signal to a display.

6. The system according to claim 1, wherein the processing circuitry is configured to render a map to a display based on electrical activity of the mid field signal at various locations on the tissue surface.

7. The system according to claim 1, wherein the processing circuitry is configured to output a diagnostic decision based on at least one characteristic of the mid-field signal.

8. The system according to claim 1, wherein the tissue surface includes any of the following: an endocardial tissue surface; an epicardial tissue surface; and an organ tissue surface.

9. An electrophysiological analysis method, comprising:

receiving unipolar signals from individual ones of a plurality of the sensing electrodes of at least one catheter configured to be inserted into a body-part having a tissue surface, the sensing electrodes being configured to contact and receive electrical signals from the tissue surface;

computing a combined far-field and mid-field signal based on summing and filtering the received unipolar signals from at least a pair of the plurality of sensing electrodes, the at least a pair of sensing electrodes being disposed around a point of interest;

computing a far-field signal as a weighted average of the received unipolar signals, weighted according to respective distances of the sensing electrodes from the point of interest; and computing and outputting a mid-field signal, representative of electrical activity below the tissue surface at the point of interest, based on subtracting the computed far-field signal from the computed combined far-field and mid-field signal.

10. The method according to claim 9, further comprising applying a high-pass filter to the sum of the received unipolar signals received from the at least a pair of the sensing electrodes.

11. The method according to claim 9, further comprising:

selecting a plurality of electrode groups from the sensing electrodes;

summing, for each one electrode group of the plurality of electrode groups, the unipolar signals received from the one electrode group, yielding a plurality of summed group signals; and computing the weighted average based on averaging the summed group signals weighted according to respective distances of the sensing electrodes from the point of interest.

12. The method according to claim 11, further comprising applying a high-pass filter to each of the summed group signals prior to computing the weighted average.

13. The method according to claim 9, further comprising rendering the mid-field signal to a display.

14. The method according to claim 9, further comprising rendering a map to a display based on electrical activity of the mid field signal at various locations on the tissue surface.

15. The method according to claim 9, further comprising outputting a diagnostic decision based on at least one characteristic of the mid-field signal.

16. The method according to claim 9, wherein the tissue surface includes any of the following: an endocardial tissue surface; an epicardial tissue surface; and an organ tissue surface.

17. A software product, comprising a non-transient computer-readable medium in which program instructions are stored, which instructions, when read by a central processing unit (CPU), cause the CPU to:

receive unipolar signals from individual ones of a plurality of the sensing electrodes of at least one catheter configured to be inserted into a body-part having a tissue surface, the sensing electrodes being configured to contact and receive electrical signals from the tissue surface;

compute a combined far-field and mid-field signal based on summing and filtering the received unipolar signals from at least a pair of the plurality of sensing electrodes, the at least a pair of the sensing electrodes being disposed around a point of interest;

compute a far-field signal as a weighted average of the received unipolar signals, weighted according to respective distances of the sensing electrodes from the point of interest; and compute and output a mid-field signal, representative of electrical activity below the tissue surface at the point of interest, based on subtracting the computed far-field signal from the computed combined far-field and mid-field signal.

18. The software product according to claim 17, wherein the instructions further cause the CPU to apply a high-pass filter to the sum of the received unipolar signals received from the at least a pair of the sensing electrodes.

19. The software product according to claim 17, wherein the instructions further cause the CPU to:

select a plurality of electrode groups from the sensing electrodes;

sum, for each one electrode group of the plurality of electrode groups, the unipolar signals received from the one electrode group, yielding a plurality of summed group signals; and compute the weighted average based on averaging the summed group signals weighted according to respective distances of the sensing electrodes from the point of interest.

20. The software product according to claim 19, wherein the instructions further cause the CPU to apply a high-pass filter to each of the summed group signals prior to computing the weighted average.

* * * * *